US012799460B2

(12) United States Patent
Mee et al.

(10) Patent No.: US 12,799,460 B2
(45) Date of Patent: Nov. 17, 2026

(54) iPSC INDUCTION

(71) Applicant: Roslin Technologies Limited, Edinburgh Midlothian (GB)

(72) Inventors: Patrick Joe Mee, Midlothian (GB); Melany Jackson, Midlothian (GB); Ryan Taylor, Midlothian (GB)

(73) Assignee: Roslin Technologies Limited, Edinburgh Midlothian (GB)

( * ) Notice: Subject to any disclaimer, the term of this patent is extended or adjusted under 35 U.S.C. 154(b) by 743 days.

(21) Appl. No.: 17/995,969

(22) PCT Filed: Apr. 16, 2021

(86) PCT No.: PCT/EP2021/059909
§ 371 (c)(1),
(2) Date: Oct. 11, 2022

(87) PCT Pub. No.: WO2021/209599
PCT Pub. Date: Oct. 21, 2021

(65) Prior Publication Data

US 2023/0313148 A1 Oct. 5, 2023

(30) Foreign Application Priority Data

Apr. 16, 2020 (EP) .................................... 20169933
Oct. 21, 2020 (GB) .................................... 2016690
Nov. 5, 2020 (GB) .................................... 2017501

(51) Int. Cl.
*C12N 5/074* (2010.01)
*C12N 15/86* (2006.01)

(52) U.S. Cl.
CPC ........... *C12N 5/0696* (2013.01); *C12N 15/86* (2013.01); *C12N 2501/603* (2013.01); *C12N 2501/606* (2013.01); *C12N 2506/08* (2013.01); *C12N 2710/24143* (2013.01)

(58) Field of Classification Search
None
See application file for complete search history.

(56) References Cited

U.S. PATENT DOCUMENTS 8,058,065 B2 * 11/2011 Yamanaka ........... C12N 5/0696 435/373
12,104,168 B2 10/2024 Szczerbinska et al.
2016/0369242 A1 12/2016 Lavial et al.

FOREIGN PATENT DOCUMENTS

CN 102317448 A 1/2012
CN 106459909 A 2/2017
WO WO-2009007852 A2 1/2009
WO WO 2010/111409 9/2010
WO WO 2016/204298 12/2016
WO WO-2016204298 A1 * 12/2016 ............ C12N 15/09

OTHER PUBLICATIONS

Esteban MA, Xu J, Yang J, Peng M, Qin D, Li W, Jiang Z, Chen J, Deng K, Zhong M, Cai J, Lai L, Pei D. Generation of induced pluripotent stem cell lines from Tibetan miniature pig. J Biol Chem. Jun. 26, 2009;284(26):17634-40. doi: 10.1074/jbc.M109.008938. PMID: 19376775; PMCID: PMC271940 (Year: 2009).*

Baird et al., Derivation of Canine Induced Pluripotent Stem Cells. Reprod Domest Anim. Aug. 2015;50(4):669-76.

Ban et al., Efficient generation of transgene-free human induced pluripotent stem cells (iPSCs) by temperature-sensitive Sendai virus vectors. Proc Natl Acad Sci U S A. Aug. 23, 2011;108(34):14234-9.

Beers et al., A cost-effective and efficient reprogramming platform for large-scale production of integration-free human induced pluripotent stem cells in chemically defined culture. Sci Rep. Jun. 11, 2015:5:11319. 9 pages.

Fu et al., Comparison of reprogramming factor targets reveals both species-specific and conserved mechanisms in early iPSC reprogramming. BMC Genomics. Dec. 22, 2018;19(1):956. 13 pages.

Fujie et al., New type of Sendai virus vector provides transgene-free iPS cells derived from chimpanzee blood. PLoS One. Dec. 5, 2014;9(12):e113052. 19 pages.

Fusaki et al., Efficient induction of transgene-free human pluripotent stem cells using a vector based on Sendai virus, an RNA virus that does not integrate into the host genome. Proc Jpn Acad Ser B Phys Biol Sci. 2009;85(8):348-62.

Kawagoe et al., Morphological features of iPS cells generated from Fabry disease skin fibroblasts using Sendai virus vector (SeVdp). Mol Genet Metab. Aug. 2013;109(4):386-9.

Kishino et al., Generation of Induced Pluripotent Stem Cells from Human Peripheral T Cells Using Sendai Virus in Feeder-free Conditions. J Vis Exp. Nov. 11, 2015:(105):53225. 5 pages.

MacArthur et al., Generation and comprehensive characterization of induced pluripotent stem cells for translational research. Regen Med. Jun. 2019;14(6):505-524.

Nishimura et al., Simple and effective generation of transgene-free induced pluripotent stem cells using an auto-erasable Sendai virus vector responding to microRNA-302. Stem Cell Res. Aug. 2017:23:13-19.

Okita et al., A more efficient method to generate integration-free human iPS cells. Nat Methods. May 2011;8(5):409-12.

Omole et al., Ten years of progress and promise of induced pluripotent stem cells: historical origins, characteristics, mechanisms, limitations, and potential applications. PeerJ. May 11, 2018:6:e4370.47 pages.

Ono et al., Generation of induced pluripotent stem cells from human nasal epithelial cells using a Sendai virus vector. PLoS One. 2012;7(8):e42855. 7 pages.

(Continued)

*Primary Examiner* — Anna Skibinsky
*Assistant Examiner* — Catherine L McCormick
(74) *Attorney, Agent, or Firm* — Foley Hoag LLP

(57) ABSTRACT

A method of inducing pluripotency in somatic cells derived from a non-human domestic animal or farm animal comprises culturing neural stem cells (NSCs) in the presence of vectors that express one or more reprogramming factors. Canine, porcine and bovine iPSCs are obtained with distinct genetic marker profiles.

8 Claims, 9 Drawing Sheets

Specification includes a Sequence Listing.

(56) References Cited

OTHER PUBLICATIONS

Seki et al., Generation of induced pluripotent stem cells from a small amount of human peripheral blood using a combination of activated T cells and Sendai virus. Nat Protoc. Mar. 15, 2012;7(4):718-28.
Shimada et al., Generation of canine induced pluripotent stem cells by retroviral transduction and chemical inhibitors. Mol Reprod Dev. Jan. 2010;77(1):2. 1 page.
Tai et al., Reprogramming human dermal fibroblast into induced pluripotent stem cells using nonintegrative Sendai virus for transduction. Malays J Pathol. Dec. 2018;40(3):325-329.
Takahashi et al., Induction of pluripotent stem cells from adult human fibroblasts by defined factors. Cell. Nov. 30, 2007;131(5):861-72.
Takahashi et al., Induction of pluripotent stem cells from mouse embryonic and adult fibroblast cultures by defined factors. Cell. Aug. 25, 2006;126(4):663-76.
Teshigawara et al., Mechanism of human somatic reprogramming to iPS cell. Lab Invest. Oct. 2017;97(10):1152-1157.
Yamanaka et al., Nuclear reprogramming to a pluripotent state by three approaches. Nature. Jun. 10, 2010;465(7299):704-12.
Ye et al., Efficient Generation of Non-Integration and Feeder-Free Induced Pluripotent Stem Cells from Human Peripheral Blood Cells by Sendai Virus. Cell Physiol Biochem. 2018;50(4):1318-1331.
Yuan et al., A six-inhibitor culture medium for improving naïve-type pluripotency of porcine pluripotent stem cells. Cell Death Discov. Jun. 17, 2019:5:104. 14 pages.
International Search Report and Written Opinion for PCT/EP2021/059909. Mailed May 7, 2021. 12 pages.
Chow et al., Safety and immune regulatory properties of canine induced pluripotent stem cell-derived mesenchymal stem cells. Stem Cell Res. Dec. 2017;25:221-232.
Congras et al., Non integrative strategy decreases chromosome instability and improves endogenous pluripotency genes reactivation in porcine induced pluripotent-like stem cells. Sci Rep. Jun. 1, 2016;6:27059. 17 pages.
Islam et al., Sendai virus-mediated expression of reprogramming factors promotes plasticity of human neuroblastoma cells. Cancer Sci. Oct. 2015;106(10):1351-61.
Koh et al., From "ES-like" cells to induced pluripotent stem cells: a historical perspective in domestic animals. Theriogenology. Jan. 1, 2014;81(1):103-11.
Okita et al., Generation of germline-competent induced pluripotent stem cells. Nature. Jul. 19, 2007;448(7151):313-7.
Tsukamoto et al., Generation of Footprint-Free Canine Induced Pluripotent Stem Cells Using Auto-Erasable Sendai Virus Vector. Stem Cells Dev. Nov. 15, 2018;27(22):1577-1586.
Zhao et al., Immunogenicity of induced pluripotent stem cells. Nature. May 13, 2011;474(7350):212-5.
"CytoTune™-iPS 2.0 Sendai Reprogramming Kit User Guide", Thermo Fisher Scientific, 2020, pp. 1-69.
Fujishiro S-H., et al., "Generation of Induced Pluripotent Stem Cells from Monkey and Pig Fibroblasts", The Journal of Gene Medicine, 2012, vol. 14, pp. 652-730, p. 657, OR-8.
Fujishiro S-H, et al., "Generation of Naive-like Porcine-induced Pluripotent Stem Cells Capable of Contributing to Embryonic and Fetal Development", Stem Cells and Development, Feb. 1, 2013, vol. 22, No. 3, pp. 473-482.
Kim J.B., et al., "Oct4-Induced Pluripotency in Adult Neural Stem Cells", Cell, Feb. 6, 2009, vol. 136, No. 3, pp. 411-419.
Nishino K., et al., "Epigenetic-Scale Comparison of Human iPSCs Generated by Retrovirus, Sendai Virus or Episomal Vectors", Regenerative Therapy, Sep. 1, 2018, vol. 9, pp. 71-78.
Ezashi T., et al., "Induced Pluripotent Stem Cells from Pigs and Other Ungulate Species: an Alternative to Embryonic Stem Cells?", Reproduction in Domestic Animals, Aug. 2012, vol. 47 (Suppl 4), pp. 92-97. doi: 10.1111/j.1439-0531.2012.02061.x. PMID: 22827356.
Ma Y., et al., "Preserving Self-renewal of Porcine Pluripotent Stem Cells in Serum-free 3i Culture Condition and Independent of LIF and b-FGF Cytokines", Cell Death Discovery, 2018, vol. 4, No. 21, pp. 1-14, https://doi.org/10.1038/s41420-017-0015-4.

* cited by examiner iPSC INDUCTION

STATEMENT OF RELATED APPLICATIONS

This application is a national phase application under 35 U.S.C. § 371 of PCT International Application No. PCT/EP2021/059909, filed on Apr. 16, 2021, which claims the benefit of GB Patent Application No. 2017501.4, filed Nov. 5, 2020, GB Patent Application No. 2016690.6, filed Oct. 21, 2020, and EP patent application No. 20169933.7, filed Apr. 16, 2020, the contents of each of which are incorporated by reference herein.

SEQUENCE LISTING

The computer readable sequence listing filed herewith, titled "SCHLI-41347-251_SQL", created Sep. 27, 2022, having a file size of 4,050 bytes, is hereby incorporated by reference in its entirety.

INTRODUCTION

The present invention relates to the production of induced pluripotent stem cells in domesticated animals and farm animals.

BACKGROUND TO THE INVENTION

The generation of induced pluripotent stem cells (iPSCs) from human and mouse primary cells is well established and routine in many laboratories. These cells grow indefinitely in culture and differentiate into derivatives of the three germ layers and are of great scientific, medical and economic importance.

Pluripotency in relation to a stem cell refers to the ability of the stem cell to form cells of all three of the somatic cell lineages: mesoderm, endoderm and ectoderm. A pluripotent stem cell is therefore capable of acting as a progenitor for all cell types found in the adult organism. This definition is not to be confused with multipotency, which in relation to a stem cell indicates it has the capacity to form daughter cells of a restricted number of somatic cell types.

In humans, it has been shown that somatic cell treatment with Oct4 and Nanog alone is enough to generate iPSCs (WO 2010/111,409).

Much effort has been placed on the generation of similar iPSCs from large domesticated animals and farm animals, such as horses, dogs, cats, pigs, sheep and cattle. It is hoped these cells will provide similar benefits in animal research and for the veterinary medical industry.

The production of iPSCs from these species has, until now, utilized integrating retroviral or lentiviral vectors (see e.g. WO 2016/204,298; and Koh and Piedrahita, 2014. "From ES-like cells to induced pluripotent stem cells: A historical perspective in domestic animals". Theriogenology 81:103-111). These methods involve the integration of vector sequences into the host genome which causes several problems, including creating unpredictable mutations, uncontrolled silencing of exogenous factors, unregulated expression of residual transgenes and strong immunogenicity (Okita et al., 2007. "Generation of germline-competent induced pluripotent stem cells". Nature 448:313-317; Zhao et al., 2011. "Immunogenicity of induced pluripotent stem cells". Nature 474:212-251). In an attempt to solve these problems, non-integrating vectors have been used to generate iPSCs from domestic animals and farm animals. Unfortunately, however, non-integrating vectors have shown to be much less effective in domestic animals and farm animals, producing only very rare and difficult to maintain, purported iPSC clones capable of being taken forward for analysis (see e.g. Tsukamoto et al. 2018). Furthermore, these clones were identified as having undesirable phenotypes (Congras et al., 2016. "Non integrative strategy decreases chromosome instability and improves endogenous pluripotency genes reactivation in porcine induced pluripotent-like stem cells". Scientific Reports 6:27059; Chow., 2017. "Safety and immune regulatory properties of canine induced pluripotent stem cell-derived mesenchymal stem cells". Stem Cell Research 25:221-232).

Fibroblasts are most commonly used as the somatic starting material in the preparation of iPSCs, this is true for humans and non-human animals alike. This is because the cells can be derived from tissue that is easily accessible in the least invasive manner, and these primary cells can be expanded sufficiently in culture prior to senescence. Other somatic starting material that requires derivation using more invasive procedures is usually avoided due to the adverse effects on the subject. Where autologous therapy is concerned, certain somatic starting material, e.g. cells from the brain, is generally considered off-limits due to the risk of death associated with the derivation procedure.

There is therefore a need for an improved method of producing iPSCs from domestic animals and farm animals that avoids both the disadvantages of utilizing integrative vectors and the inefficiencies associated with current methods utilizing non-integrative vectors.

An object of the invention is thus to provide an efficient and effective method of inducing pluripotency in a somatic cell from a domestic animal or a farm animal. In specific embodiments, the invention aims to provide alternative and preferably improved methods of iPSC derivation, of canine and porcine iPSCs in particular, and also aims to provide the iPSCs per se.

SUMMARY OF THE INVENTION

The invention provides a method of inducing pluripotency, comprising culturing neural stem cells (NSCs) in the presence of vectors that express one or more reprogramming factors, wherein the NSCs are derived from a domestic animal or a farm animal.

The invention also provides a method of inducing pluripotency, comprising culturing somatic cells of lower relative potency in the presence of non-integrating vectors that express one or more reprogramming factors, wherein the cells are derived from a domestic animal or a farm animal.

The induced pluripotent stem cells (iPSCs) generated by methods according to the invention also form part of the invention. The invention hence also provides iPSCs with unique marker profiles.

DETAILS OF THE INVENTION

Accordingly, the present invention provides a method of inducing pluripotency, comprising culturing neural stem cells (NSCs) in the presence of vectors that express one or more reprogramming factors, wherein the NSCs are derived from a domestic animal or a farm animal.

The farm animal and/or domestic animal is non-human; it is preferably selected from dogs, cats, cattle, sheep, pigs, goats, horses, chickens, guinea pigs, donkeys, deer, ducks, geese, camels, llamas, alpacas, turkeys, rabbits and hamsters.

The somatic NSCs are more preferably derived from dogs (canine), cattle (bovine), sheep (ovine), pigs (porcine) and horses (equine); they are derived in particular embodiments from dogs, pigs, cattle and horses, and from dogs and pigs and cattle in specific examples below.

Using the invention, iPSCs from domestic and farm animals have been obtained efficiently and with demonstrable confirmation of pluripotency. The reprogramming efficiency is surprisingly and advantageously higher when using NSCs as the starting material for inducing pluripotency, compared with using fibroblasts as the starting material. This increased reprogramming efficiency is apparent through the generation of thousands of iPSC clones when starting from NSCs, as opposed to just a few purported iPSC clones when starting from fibroblasts.

As set out in more detail below in examples, iPSCs from dog, pig and cow have successfully been derived and maintained in culture according to the invention.

It is an advantage of the iPSCs of the invention that self-renewing capacity is maintained during expansion. It is observed in the examples that the canine, porcine and/or bovine iPSCs maintain their morphology (generating smooth-edged colonies) and their ability to differentiate into derivatives of all three germ layers over successive passages. iPSCs are obtainable that maintain their ability to differentiate into derivatives of the three germ layers after at least 40 cell culture passages, preferably at least 50 passages, preferably at least 100 passages, more preferably at least 200 passages, or even more preferably at least 1000 passages.

The vectors are preferably non-integrating vectors. It is preferred that the non-integrating vectors are selected from adenoviral vectors, adeno-associated viral vectors, respiroviral vectors, integration-deficient retro-lentiviral vectors, poxviral vectors, episomal vectors, plasmid vectors and artificial chromosome vectors. An advantage of the resultant iPSCs is absence of unwanted, and potentially confounding, integrated genetic material in progeny of the iPSCs. Preferably, the non-integrating vector is a Sendai virus.

The reprogramming factors expressed by the vectors are preferably selected from two or more or all of Oct4, Sox2, cMyc and Klf4. It is preferred that the somatic cells are cultured with vectors expressing all the reprogramming factors; in examples below all factors were used for canine and porcine iPSCs. Optionally, a reduced number of factors are used in combination; for example, Oct4 may be used in combination with Sox2 and/or cMyc, or especially in combination with KLF4. Preferably, at least Oc4 and cMyc are present. In any case, when using a combination of factors, each reprogramming factor may be expressed on the same vector or on different vectors. In a particularly preferred embodiment, the somatic cells are cultured with three vector preparations, wherein the first expresses polycistronic Klf4—Oct3/4—Sox2, the second expresses cMyc, and the third expresses Klf4. This has been found to provide a ratio of the factors amenable to derivation of pluripotent cells.

The iPSCs generated according to the methods of the invention are suitably cultured in a knockout serum replacement (KOSR) medium.

Following successful induction of pluripotency according to the invention, the iPSCs benefit from diminishing levels of viral vector over successive passage rounds. This is a major benefit of using a non-integrating vector. It is preferred that the iPSC population (comprising e.g. at least $10^6$ cells, suitably at least $10^8$ cells or preferably at least $10^{10}$ cells) reach a purity wherein less than 1% of the original vector concentration is present in the population, preferably less than 0.1%, or more preferably less than 0.01%. The original vector concentration may be defined as the concentration of vector present in the iPSC population at passage 1 in the cell culture. In specific embodiments of the invention, iPSC populations are obtained that are substantially vector free.

Hitherto the art has failed to derive and reliably maintain iPSCs from the animal species of the present invention. Herein, it has been found that iPSCs are advantageously derived and maintained using medium supplements. It is preferred that the iPSC growth medium comprises a gp130 agonist.

Preferably, the gp130 agonist is leukemia inhibitory factor (LIF). Alternatively, the gp130 signalling pathway can be stimulated using other available and known agonists, including IL-6, cardiotrophin 1(CT-1), ciliary neurotrophic factor (CNTF), oncostatin M (OSM), and IL-11. It is separately preferred that the iPSC growth medium comprises an FGF receptor agonist. Preferably, the FGF receptor agonist is basic fibroblast growth factor (bFGF). Again, other agonists are known and commercially available. A preferred medium comprises both a gp130 agonist and an FGF receptor agonist, and this combination was successfully used in examples below.

Optionally, the iPSCs are cultured in a growth medium comprising a GSK3 inhibitor. Preferably, the GSK3 inhibitor is selected from insulin, SB216763, SB415286, azakenpaullone, AR-A0144, a bis-7-azaindolylmaleimide, BIO, CHIR-98014, CHIR-99021, TWS119, A1070722, TDZD8 and AZD1080. Preferably, the GSK3 inhibitor is CHIR-99021. Good results have been obtained in using the GSK3 inhibitor for both porcine and canine iPSCs, especially porcine iPSCs.

It is further advantageous to maintain the iPSCs on a feeder layer of cells, generally an adherent layer of somatic feeder cells, preferably non-human feeder cells. The iPSCs of examples are cultured in the presence of a feeder layer of irradiated mouse embryonic fibroblast feeders (MEFs).

The invention also provides a method of inducing pluripotency, comprising culturing somatic cells in the presence of non-integrating vectors that express one or more reprogramming factors, wherein the cells are derived from a domestic animal or a farm animal.

The farm animal and/or domestic animal is non-human and preferably selected from dogs, cats, cattle, sheep, pigs, goats, horses, chickens, guinea pigs, donkeys, ducks, geese, camels, llamas, alpacas, turkeys, rabbits, and hamsters. Very suitable animals are dogs, cattle, sheep, pigs and horses.

Preferably, the farm animal is pig, cattle, sheep or horse (i.e. is porcine, bovine, ovine or equine).

Preferably, the domestic animal is a dog (i.e. is canine).

Preferably, the somatic cells are NSCs.

The reprogramming factors expressed by the vectors are preferably as described elsewhere herein, e.g. are selected from Oct4, Sox2, cMyc, and Klf4.

It is also preferred that the non-integrating vectors are as described elsewhere herein, preferably, the non-integrating vector being a Sendai virus.

Medium is again suitably as described elsewhere herein. Hence, the iPSCs are preferably cultured in a knockout serum replacement (KOSR) medium, it is preferred that the iPSC growth medium comprises a gp130 agonist, preferably, LIF, and it is further preferred that the iPSC growth medium comprises an FGF receptor agonist. Optionally, the iPSCs are cultured in a growth medium comprising a GSK3 inhibitor. Preferably, the GSK3 inhibitor is selected from insulin, SB216763, SB415286, azakenpaullone, AR-A0144, a bis-7-azaindolylmaleimide, BIO, CHIR-98014, CHIR- 99021, TWS119, A1070722, TDZD8 and AZD1080. Preferably, the GSK3 inhibitor is CHIR-99021.

The iPSCs are preferably cultured in the presence of a feeder layer of cells, also as described elsewhere herein.

The methods of the invention, described above and below, are able to produce thousands of successful iPSC clones. The high transduction efficiency observed is significantly advantageous, hence providing an improved method of iPSC production from somatic cells derived from farm animals and domestic animals. Based on art methods, iPSC derivation was estimated to be approximately 1000 fold more efficient using the methods of the invention.

The invention thus also provides iPSCs per se obtainable according to the methods described above and below. Preferably, the iPSCs are positive for the pluripotency markers NANOG, REX1, SSEA-3 and SSEA-4.

In a preferred embodiment, the invention provides an iPSC from a farm animal or a domestic animal, wherein the iPSC is positive for the pluripotency markers NANOG, REX1, SSEA-3 and SSEA-4. Preferably the iPSCs are provided as isolated cells.

iPSCs of the invention are suitably characterised by high levels of expression of SSEA-3 and SSEA-4. In populations of cells according to the invention, preferably 50% or greater of the cells express SSEA-3 and 50% or greater of the cells express SSEA-4. These populations generally include many tens of thousands or hundreds of thousands or millions of cells, and suitably include at least 102, at least 103 or at least $10^5$ cells. More preferably greater that 60% of the cells are positive for SSEA-4 and 60% or greater of the cells are positive for SSEA-3. In embodiments described in more detail below, in excess of 60% of the iPSCs were positive for SSEA-4 expression while in excess of 50% of that SSEA-$4^+$ population of iPSCs were also SSEA-$3^+$.

It is preferred that the iPSCs of the invention are positive for one or more, two or more, three or more, or all of GLDN, PTK2B, LOC110260197, ANGPT1, LY96, NYAP2, THBS2, ULK4, CRSP3, CHST8, SKOR1, KCNMB2, LMNA, HTRA1, PHLDA1, FGF1 and GASK1B expression.

More preferably, the iPSCs are positive for one or more, two or more, three or more, or all of LMNA, HTRA1, PHLDA1, FGF1 and GASK1B expression. Indeed, most preferably, the iPSCs express all of these genetic markers.

In populations of iPSCs according to the invention, preferably 50% or greater of the cells express LMNA, more preferably 60% or greater of the cells express LMNA, more preferably 70% or greater of the cells express LMNA, more preferably 80% or greater of the cells express LMNA, more preferably 90% or greater of the cells express LMNA, and most preferably 95% or greater of the cells express LMNA.

In populations of iPSCs according to the invention, preferably 50% or greater of the cells express HTRA1, more preferably 60% or greater of the cells express HTRA1, more preferably 70% or greater of the cells express HTRA1, more preferably 80% or greater of the cells express HTRA1, more preferably 90% or greater of the cells express HTRA1, and most preferably 95% or greater of the cells express HTRA1.

In populations of iPSCs according to the invention, preferably 50% or greater of the cells express PHLDA1, more preferably 60% or greater of the cells express PHLDA1, more preferably 70% or greater of the cells express PHLDA1, more preferably 80% or greater of the cells express PHLDA1, more preferably 90% or greater of the cells express PHLDA1, and most preferably 95% or greater of the cells express PHLDA1.

In populations of iPSCs according to the invention, preferably 50% or greater of the cells express FGF1, more preferably 60% or greater of the cells express FGF1, more preferably 70% or greater of the cells express FGF1, more preferably 80% or greater of the cells express FGF1, more preferably 90% or greater of the cells express FGF1, and most preferably 95% or greater of the cells express FGF1.

In populations of iPSCs according to the invention, preferably 50% or greater of the cells express GASK1B, more preferably 60% or greater of the cells express GASK1B, more preferably 70% or greater of the cells express GASK1B, more preferably 80% or greater of the cells express GASK1B, more preferably 90% or greater of the cells express GASK1B, and most preferably 95% or greater of the cells express GASK1B.

In populations of iPSCs according to the invention, preferably 50% or greater of the cells express LMNA, HTRA1, PHLDA1, FGF1 and GASK1B, more preferably 60% or greater of the cells express LMNA, HTRA1, PHLDA1, FGF1 and GASK1B, more preferably 70% or greater of the cells express LMNA, HTRA1, PHLDA1, FGF1 and GASK1B, more preferably 80% or greater of the cells express LMNA, HTRA1, PHLDA1, FGF1 and GASK1B, more preferably 90% or greater of the cells express LMNA, HTRA1, PHLDA1, FGF1 and GASK1B, and most preferably 95% or greater of the cells express LMNA, HTRA1, PHLDA1, FGF1 and GASK1B.

It is an advantage of the iPSCs of the invention that the specific marker expression is maintained during expansion. It is observed in the examples that the canine, bovine and/or porcine iPSCs maintain their morphology (generating smooth-edged colonies) and their ability to differentiate into derivatives of all three germ layers over successive passages. iPSCs are obtainable that maintain expression of LMNA, HTRA1, PHLDA1, FGF1 and GASK1B after at least 10 cell culture passages, preferably at least 20 passages, preferably at least 50 passages, more preferably at least 100 passages, or even more preferably at least 1000 passages.

In embodiments of the invention, the iPSCs are from dogs, pigs, cattle, horses or sheep. Preferably, the iPSC is a canine, a bovine or a porcine iPSC. Preferably, the iPSC is a canine or a porcine iPSC.

In specific embodiments of the invention, described in more detail below, in excess of 60% of canine iPSCs and in excess of 80% of porcine iPSCs were positive for SSEA-4 expression, while of that SSEA-$4^+$ population of iPSCs in excess of 55% of the canine iPSCs were also SSEA-$3^+$ and in excess of 50% of the porcine iPSCs were also SSEA-$3^+$. The canine and porcine iPSCs were also positive for Rex1 and Nanog.

The invention also provides using the iPSCs in medical/veterinary therapy. Preferably, the therapy is an allogeneic cell-based therapy. This is advantageous in that the somatic starting material for iPSC production need not be derived from the recipient of the therapy.

EXAMPLES

The present invention is now described in more and specific details in relation to the production of specific induced pluripotent stem cells (iPSCs) and with reference to the accompanying drawings in which.

Figure 1:
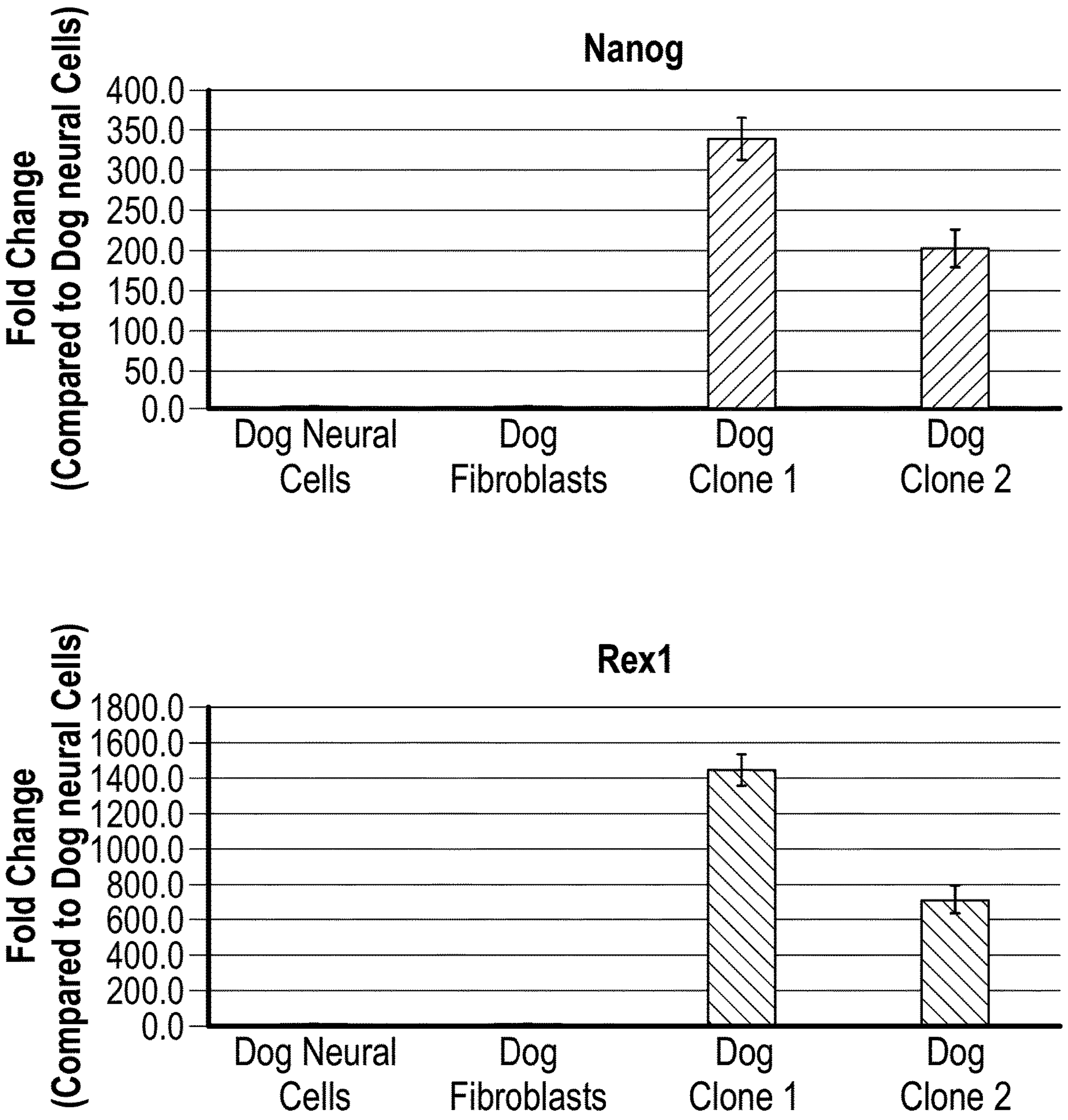
FIG. 1 shows NANOG and REX1 expression in canine iPSCs.

DNA, RNA and amino acid sequences are referred to below, in which:

SEQ ID NO: 1 is the porcine LMNA forward primer DNA sequence;

SEQ ID NO: 2 is the porcine LMNA reverse primer DNA sequence;

SEQ ID NO: 3 is the canine LMNA forward primer DNA sequence;

SEQ ID NO: 4 is the canine LMNA reverse primer DNA sequence;

SEQ ID NO: 5 is the porcine HTRA1 forward primer DNA sequence;

SEQ ID NO: 6 is the porcine HTRA1 reverse primer DNA sequence;

SEQ ID NO: 7 is the canine HTRA1 forward primer DNA sequence;

SEQ ID NO: 8 is the canine HTRA1 reverse primer DNA sequence;

SEQ ID NO: 9 is the porcine FGF1 forward primer DNA sequence;

SEQ ID NO: 10 is the porcine FGF1 reverse primer DNA sequence;

SEQ ID NO: 11 is the canine FGF1 forward primer DNA sequence;

SEQ ID NO: 12 is the canine FGF1 reverse primer DNA sequence;

SEQ ID NO: 13 is the porcine GASK1B forward primer DNA sequence;

SEQ ID NO: 14 is the porcine GASK1B reverse primer DNA sequence;

SEQ ID NO: 15 is the canine GASK1B forward primer DNA sequence;

SEQ ID NO: 16 is the canine GASK1B reverse primer DNA sequence;

SEQ ID NO: 17 is the porcine PHLDA1 forward primer DNA sequence;

SEQ ID NO: 18 is the porcine PHLDA1 reverse primer DNA sequence;

SEQ ID NO: 19 is the canine PHLDA1 forward primer DNA sequence; and

SEQ ID NO: 20 is the canine PHLDA1 reverse primer DNA sequence.

Example 1—Derivation of Primary Canine Neural Stem Cells

Neural stem cells (NSCs) were derived from the brain of a 6-year-old dog.

A large sandwich box was washed, cleaned and transferred to a class II cabinet before being sprayed with 70% industrial methylated spirit and left to air dry. The UV light was turned on and the box left for 20 minutes. Separately, two 10 $cm^2$ tissue culture dishes were re-coated with iMatrix Laminin 511 and stored at 4 °C overnight.

Upon receipt, the canine brain was placed in the sterile sandwich box in phosphate buffered saline (PBS) without calcium and magnesium. The brain was cut in half into its two lobes using a scalpel. The area of the brain comprising the subventricular zone (lining the lateral ventricles of the forebrain) was isolated.

The excised subventricular zone was cut into smaller pieces that were then placed into a 50 ml tube with 10 ml accutase. Shaking intermittently, the tube was incubated for 10 minutes at 37 °C. A pipette was then used to help dissociate the cells from the tissue. 20 ml PBS was added to the tube and the larger pieces of tissue were allowed to settle at the bottom of the tube, before the supernatant was removed and placed into a fresh tube. The accutase process was then repeated in the tube with the larger pieces of tissue.

The fresh tubes comprising supernatant were centrifuged at 1800 rpm for 4 minutes. The resulting supernatant in these tubes was removed and resuspended in 10 ml PBS, before being passed through a 70 μm cell strainer. The cells were then plated out into two 10 $cm^2$ laminin coated dishes (each with 20 ml RHB-A medium+10 ng/ml huEGF+10 ng/ml HuFGF+penicillin, dihydrostreptomycin and primocin).

The growth media was replaced every 1-2 days until the cultures were around 70% confluent (around 9-14 days). Each dish was then split into two 75 $cm^2$ laminin coated flasks.

NSC morphology was assessed via microscopy; the cells appeared to grow as single cells but, as they became more confluent, looked like a network with thin dendritic processes.

Before Culture Day 20, the NSCs were frozen down in vials according to standard laboratory practice.

Example 2—Derivation of Primary Porcine Neural Stem Cells

Neural stem cells (NSCs) were derived from the brain of a 1-day-old piglet.

A large sandwich box was washed, cleaned and transferred to a class II cabinet before being sprayed with 70% industrial methylated spirit and left to air dry. The UV light was turned on and the box left for 20 minutes. Separately, two 10 $cm^2$ tissue culture dishes were re-coated with iMatrix Laminin 511 and stored at 4 °C overnight.

Upon receipt, the porcine brain was placed in the sterile sandwich box in phosphate buffered saline (PBS) without calcium and magnesium. The brain was cut in half into its two lobes using a scalpel. The area of the brain comprising the subventricular zone (lining the lateral ventricles of the forebrain) was isolated.

The excised subventricular zone was cut into smaller pieces that were then placed into a 50 ml tube with 10 ml accutase. Shaking intermittently, the tube was incubated for 10 minutes at 37 °C. A pipette was then used to help dissociate the cells from the tissue. 20 ml PBS was added to the tube and the larger pieces of tissue were allowed to settle at the bottom of the tube, before the supernatant was removed and placed into a fresh tube. The accutase process was then repeated in the tube with the larger pieces of tissue.

The fresh tubes comprising supernatant were centrifuged at 1800 rpm for 4 minutes. The resulting supernatant in these tubes was removed and resuspended in 10 ml PBS, before being passed through a 70 μm cell strainer. The cells were then plated out into two 10 $cm^2$ laminin coated dishes (each with 20 ml RHB-A medium+10 ng/ml huEGF+10 ng/ml HuFGF+penicillin, dihydrostreptomycin and primocin).

The growth media was replaced every 1-2 days until the cultures were around 70% confluent (around 9-14 days). Each dish was then split into two 75 $cm^2$ laminin coated flasks.

NSC morphology was assessed via microscopy throughout the culture period; the cells appeared to grow as single cells but, as they became more confluent, looked like a network with thin dendritic processes.

Before Culture Day 20, the NSCs were frozen down in vials according to standard laboratory practice.

Example 3—Derivation of Primary Bovine Neural Stem Cells

Neural stem cells (NSCs) were derived from the brains of a 1-year-old cow and a 2-year-old cow (both chemically euthanized).

Two large sandwich boxes were washed, cleaned and transferred to a class II cabinet before being sprayed with 70% industrial methylated spirit and left to air dry. The UV light was turned on and the boxes left for 20 minutes. Separately, four 10 $cm^2$ tissue culture dishes were re-coated with iMatrix Laminin 511 and stored at 4 °C overnight.

Upon receipt, the bovine brains were placed in sterile sandwich boxes in phosphate buffered saline (PBS) without calcium and magnesium. The brains were cut in half into two lobes using a scalpel. The area of the brains comprising the subventricular zone (lining the lateral ventricles of the forebrain) was isolated.

The excised subventricular zone was cut into smaller pieces that were then placed into a 50 ml tube with 10 ml accutase. Shaking intermittently, the tube was incubated for 10 minutes at 37 °C. A pipette was then used to help dissociate the cells from the tissue. 20 ml PBS was added to the tube and the larger pieces of tissue were allowed to settle at the bottom of the tube, before the supernatant was removed and placed into a fresh tube. The accutase process was then repeated in the tube with the larger pieces of tissue.

The fresh tubes comprising supernatant were centrifuged at 1800 rpm for 4 minutes. The resulting supernatant in these tubes was removed and resuspended in 10 ml PBS, before being passed through a 70 μm cell strainer. The cells were then plated out into two 10 $cm^2$ laminin coated dishes (each with 20 ml RHB-A medium+10 ng/ml bovine EGF+10 ng/ml bovine FGF+penicillin, dihydrostreptomycin and primocin).

The growth media was replaced every 1-2 days until the cultures were around 70% confluent (around 9-14 days). Each dish was then split into two 75 $cm^2$ laminin coated flasks.

NSC morphology was assessed via microscopy throughout the culture period; the cells appeared to form (1) densely packed colonies without processes (like epithelial cells), (2) long stretched out cells in a looser network with dendritic processes, and (3) smaller single cells that developed into a network with thin dendritic processes as they became more confluent.

Before Culture Day 20, the NSCs were frozen down in vials according to standard laboratory practice.

Example 4—Reprogramming of Canine Neural Stem Cells

Canine neural stem cells (NSCs) were reprogrammed using the CytoTune 2.0 Reprogramming kit. This kit uses a modified, non-transmissible form of the Sendai virus delivery system to introduce reprogramming vectors into primary cells, in order to enable the generation of iPSCs. The Sendai virus used in the kit is non-integrating and remains in the cell cytoplasm. The viral particles are cleared from the cell cytoplasm over generations of cell division and can be screened for full clearance using qPCR assays.

One day before transduction, $3\times10^5$ actively growing NSCs were plated in 1 well of a 6-well plate on a laminin 511 matrix in RHB-A medium (as described in Examples 1-3). This allowed the cells to adhere and extend, as well as reach a 50-80% confluence before transduction.

The titre of each CytoTune 2.0 reprogramming vector is lot-dependent, with the lot number specific certificate of analysis (CoA) downloadable from:— https://www.thermofisher.com/order/catalog/product/A16517

The Lot specific CoA gave the volumes of viral vector per well to achieve an MOI of 5:5:3 (KOS:hc-Myc:hKlf4).

1 ml of warm RHB-A medium was provided per well of cells to be transduced. The Cytotune 2.0 vials (containing the vector) were removed from −80 °C storage and thawed by hand. The vials were centrifuged to collect the contents and then placed on ice. The calculated volume of each vector was added to the RHB-A medium in each well and then mixed with a pipette. The cells were then incubated at 37 °C for 24 hours before the transduction medium was aspirated and replaced with fresh RHB-A (1 ml per well). The RHB-A medium was then changed every 24 hours until Day 6 of the culture.

The transduced cells were harvested using 0.3 ml/well accutase for 5 minutes at 37 °C. The incubation time was adhered to due to the sensitivity of the cells to the enzyme. During dissociation (rounding-up of the cells), 2 ml of RHB-A were added to protect the cells against the enzyme. The cells were collected into 15 ml tubes and centrifuged at 200 g for 4 minutes. The cells were then resuspended in canine iPSC medium, the recipe for which is as follows:—

To a 500 ml bottle of DMEM/F12 (Thermo Fisher cat 11520396), add 100 ml KOSR (Thermo Fisher 10828028), 5 ml Non Essential Amino Acids 100× (Thermo Fisher 11140035), 5 ml Sodium Pyruvate 100 mM (Thermo Fisher 11360039), 1 ml 2-Mercaptoethanol (Thermo Fisher 31350010), and 5 ml Antibiotic antimycotic (Sigma A5955). Just prior to use, add 62 μl huFGF (Peprotech 100-18B), 62 μl huLIF (Peprotech 300-05), and 500 ul of 3 mM Chiron stock (Tolcris—final conc. 3 μM). Swirl to mix before use.

The cells were counted before being seeded into the new culture vessels and incubated. In order to optimize reprogramming efficiency, the cells were plated at a relatively high density, typically $1\times10^5$-$5\times10^5$ cells per 100 mm culture dish.

The canine iPSC culture medium was changed every 24 hours until colony formation was observed. This colony formation was typically observed within 12 days to 4 weeks.

Colonies were picked based on morphological properties. The day before picking colonies, a 24 well plate (pre-coated with 0.2% Gelatin/PBS) of irradiated mouse embryonic fibroblasts (MEF Feeder Cells) was prepared ($4\times10^6$ MEF for 24 wells) in MEF media (1 ml per well), the recipe for which is as follows:—

To a 500 ml bottle of DMEM/F12 (Thermo Fisher cat 11520396), add 50 ml FCS (Sigma F2442), 5 ml Non Essential Amino Acids 100× (Thermo Fisher 11140035), 5 ml Sodium Pyruvate 100 mM (Thermo Fisher 11360039), 1 ml 2-Mercaptoethanol (Thermo Fisher 31350010), and 5 ml Antibiotic antimycotic (Sigma A5955). Swirl to mix before use.

The picked colonies were each transferred into separate wells of the prepared 24 well plate with canine iPSC media. After colony growth, the colonies were disaggregated using accutase and re-plated in single wells of a prepared 6-well plate of irradiated MEFs. Following confluence, accutase was used and the cells were split into six wells of a prepared 6-well plate of irradiated MEFs. Following confluence, the cells were frozen down in a bank of 12 vials (half a well per vial). As such, each colony resulted in 12 vials of cells being banked.

When passaging canine iPSCs embedded in MEFs, gentle pipetting of the cells often helps to dissociate the cell types. The cell mixture can then be placed in tubes and centrifuged at 1500 rpm (0.4 rcf) for 3 minutes, before aspirating the media and resuspending the canine iPSCs in canine iPSC media. Before the cells are added to the new pre-plated MEFs, the MEF media is aspirated and replaced with canine iPSC media.

Example 5—Reprogramming of Porcine Neural Stem Cells

Porcine neural stem cells (NSCs) were reprogrammed using the CytoTune 2.0 Reprogramming kit. This kit uses a modified, non-transmissible form of the Sendai virus delivery system to introduce reprogramming vectors into primary cells, in order to enable the generation of iPSCs. The Sendai virus used in the kit is non-integrating and remains in the cell cytoplasm. The viral particles are cleared from the cell cytoplasm over generations of cell division and can be screened for full clearance using qPCR assays.

One day before transduction, $3\times10^5$ actively growing NSCs were plated in 1 well of a 6-well plate on a laminin 511 matrix in RHB-A medium (as described in Examples 1-3). This allowed the cells to adhere and extend, as well as reach a 50-80% confluence before transduction.

The titre of each CytoTune 2.0 reprogramming vector is lot-dependent, with the lot number specific certificate of analysis (CoA) downloadable from:— https://www.thermofisher.com/order/catalog/product/A16517

The Lot specific CoA gave the volumes of viral vector per well to achieve an MOI of 5:5:3 (KOS:hc-Myc:hKlf4).

1 ml of warm RHB-A medium was provided per well of cells to be transduced. The Cytotune 2.0 vials (containing the vector) were removed from −80 °C storage and thawed by hand. The vials were centrifuged to collect the contents and then placed on ice. The calculated volume of each vector was added to the RHB-A medium in each well and then mixed with a pipette. The cells were then incubated at 37 °C for 24 hours before the transduction medium was aspirated and replaced with fresh RHB-A (1 ml per well). The RHB-A medium was then changed every 24 hours until Day 6 of the culture.

The transduced cells were harvested using 0.3 ml/well accutase for 5 minutes at 37 °C. The incubation time was adhered to due to the sensitivity of the cells to the enzyme. During dissociation (rounding-up of the cells), 2 ml of RHB-A was added to protect the cells against the enzyme. The cells were collected into 15 ml tubes and centrifuged at 200 g for 4 minutes. The cells were then resuspended in porcine iPSC medium, the recipe for which is as follows:—

To a 500 ml bottle of DMEM/F12 (Thermo Fisher cat 11520396), add 100 ml KOSR (Thermo Fisher 10828028), 5 ml Non Essential Amino Acids 100× (Thermo Fisher 11140035), 5 ml Sodium Pyruvate 100 mM (Thermo Fisher 11360039), 1 ml 2-Mercaptoethanol (Thermo Fisher 31350010), and 5 ml Antibiotic antimycotic (Sigma A5955). Just prior to use, add 62 μl huFGF (Peprotech 100-18B), and 62 μl huLIF (Peprotech 300-05). Swirl to mix before use.

The cells were counted before being seeded into the new culture vessels and incubated. In order to optimize reprogramming efficiency, the cells were plated at a relatively high density, typically $1\times10^5$-$5\times10^5$ cells per 100 mm culture dish.

The porcine iPSC culture medium was changed every 24 hours until colony formation was observed. This colony formation was typically observed within 12 days to 4 weeks.

Colonies were picked based on morphological properties. The day before picking colonies, a 24 well plate (pre-coated with 0.2% Gelatin/PBS) of irradiated mouse embryonic fibroblasts (MEF Feeder Cells) was prepared ($4\times10^6$ MEF for 24 wells) in MEF media (1 ml per well), the recipe for which is as follows:—

To a 500 ml bottle of DMEM/F12 (Thermo Fisher cat 11520396), add 50 ml FCS (Sigma F2442), 5 ml Non Essential Amino Acids 100× (Thermo Fisher 11140035), 5 ml Sodium Pyruvate 100 mM (Thermo Fisher 11360039), 1 ml 2-Mercaptoethanol (Thermo Fisher 31350010), and 5 ml Antibiotic antimycotic (Sigma A5955). Swirl to mix before use.

The picked colonies were each transferred into separate wells of the prepared 24 well plate with porcine iPSC media. After colony growth, the colonies were disaggregated using accutase and re-plated in single wells of a prepared 6-well plate of irradiated MEFs. Following confluence, accutase was used and the cells were split into six wells of a prepared 6-well plate of irradiated MEFs. Following confluence, the cells were frozen down in a bank of 12 vials (half a well per vial). As such, each colony resulted in 12 vials of cells being banked.

When passaging porcine iPSCs embedded in MEFs, gentle pipetting of the cells often helps to dissociate the cell types. The cell mixture can then be placed in tubes and centrifuged at 1500 rpm (0.4 rcf) for 3 minutes, before the aspirating the media and resuspending the porcine iPSCs in porcine iPSC media. Before the cells are added to the new pre-plated MEFs, the MEF media is aspirated and replaced with porcine iPSC media.

Example 6—Reprogramming of Bovine Neural Stem Cells

Bovine neural stem cells (NSCs) were reprogrammed using the CytoTune 2.0 Reprogramming kit. This kit uses a modified, non-transmissible form of the Sendai virus delivery system to introduce reprogramming vectors into primary cells, in order to enable the generation of iPSCs. The Sendai virus used in the kit is non-integrating and remains in the cell cytoplasm. The viral particles are cleared from the cell cytoplasm over generations of cell division and can be screened for full clearance using qPCR assays.

One day before transduction, $3\times10^5$ actively growing NSCs were plated in 1 well of a 6-well plate on a laminin 511 matrix in RHB-A medium (as described in Examples 1-3). This allowed the cells to adhere and extend, as well as reach a 50-80% confluence before transduction.

The titre of each CytoTune 2.0 reprogramming vector is lot-dependent, with the lot number specific certificate of analysis (CoA) downloadable from:—https://www.thermofisher.com/order/catalog/product/A16517

The Lot specific CoA gave the volumes of viral vector per well to achieve an MOI of 5:5:3 (KOS:hc-Myc:hKlf4).

1 ml of warm RHB-A medium was provided per well of cells to be transduced. The Cytotune 2.0 vials (containing the vector) were removed from −80 °C storage and thawed by hand. The vials were centrifuged to collect the contents and then placed on ice. The calculated volume of each vector was added to the RHB-A medium in each well and then mixed with a pipette. The cells were then incubated at 37 °C for 24 hours before the transduction medium was aspirated and replaced with fresh RHB-A (1 ml per well). The RHB-A medium was then changed every 24 hours until Day 6 of the culture.

The transduced cells were harvested using 0.3 ml/well accutase for 5 minutes at 37 °C. The incubation time was adhered to due to the sensitivity of the cells to the enzyme. During dissociation (rounding-up of the cells), 2 ml of RHB-A was added to protect the cells against the enzyme. The cells were collected into 15 ml tubes and centrifuged at 200 g for 4 minutes. The cells were then resuspended in bovine iPSC medium, the recipe for which is as follows:—

To a 500 ml bottle of DMEM/F12 (Thermo Fisher cat 11520396), add 100 ml KOSR (Thermo Fisher 10828028), 5 ml Non Essential Amino Acids 100× (Thermo Fisher 11140035), 5 ml Sodium Pyruvate 100 mM (Thermo Fisher 11360039), 1 ml 2-Mercaptoethanol (Thermo Fisher 31350010), and 5 ml Antibiotic antimycotic (Sigma A5955). Just prior to use, add 62 μl huFGF (Peprotech 100-18B), and 62 μl huLIF (Peprotech 300-05). Swirl to mix before use.

The cells were counted before being seeded into the new culture vessels and incubated. In order to optimize reprogramming efficiency, the cells were plated at a relatively high density, typically $1\times10^5$-$5\times10^5$ cells per 100 mm culture dish.

The bovine iPSC culture medium was changed every 24 hours until colony formation was observed. This colony formation was typically observed within 12 days to 4 weeks.

Colonies were picked based on morphological properties. The day before picking colonies, a 24 well plate (pre-coated with 0.2% Gelatin/PBS) of irradiated mouse embryonic fibroblasts (MEF Feeder Cells) was prepared ($4\times10^6$ MEF for 24 wells) in MEF media (1 ml per well), the recipe for which is as follows:—

To a 500 ml bottle of DMEM/F12 (Thermo Fisher cat 11520396), add 50 ml FCS (Sigma F2442), 5 ml Non Essential Amino Acids 100× (Thermo Fisher 11140035), ml Sodium Pyruvate 100 mM (Thermo Fisher 11360039), 1 ml 2-Mercaptoethanol (Thermo Fisher 31350010), and 5 ml Antibiotic antimycotic (Sigma A5955). Swirl to mix before use.

The picked colonies were each transferred into separate wells of the prepared 24 well plate with bovine iPSC media. After colony growth, the colonies were disaggregated using accutase and re-plated in single wells of a prepared 6-well plate of irradiated MEFs. Following confluence, accutase was used and the cells were split into six wells of a prepared 6-well plate of irradiated MEFs. Following confluence, the cells were frozen down in a bank of 12 vials (half a well per vial). As such, each colony resulted in 12 vials of cells being banked.

When passaging bovine iPSCs embedded in MEFs, gentle pipetting of the cells often helps to dissociate the cell types. The cell mixture can then be placed in tubes and centrifuged at 1500 rpm (0.4 rcf) for 3 minutes, before the aspirating the media and resuspending the bovine iPSCs in bovine iPSC media. Before the cells are added to the new pre-plated MEFs, the MEF media is aspirated and replaced with bovine iPSC media.

Figure 9:
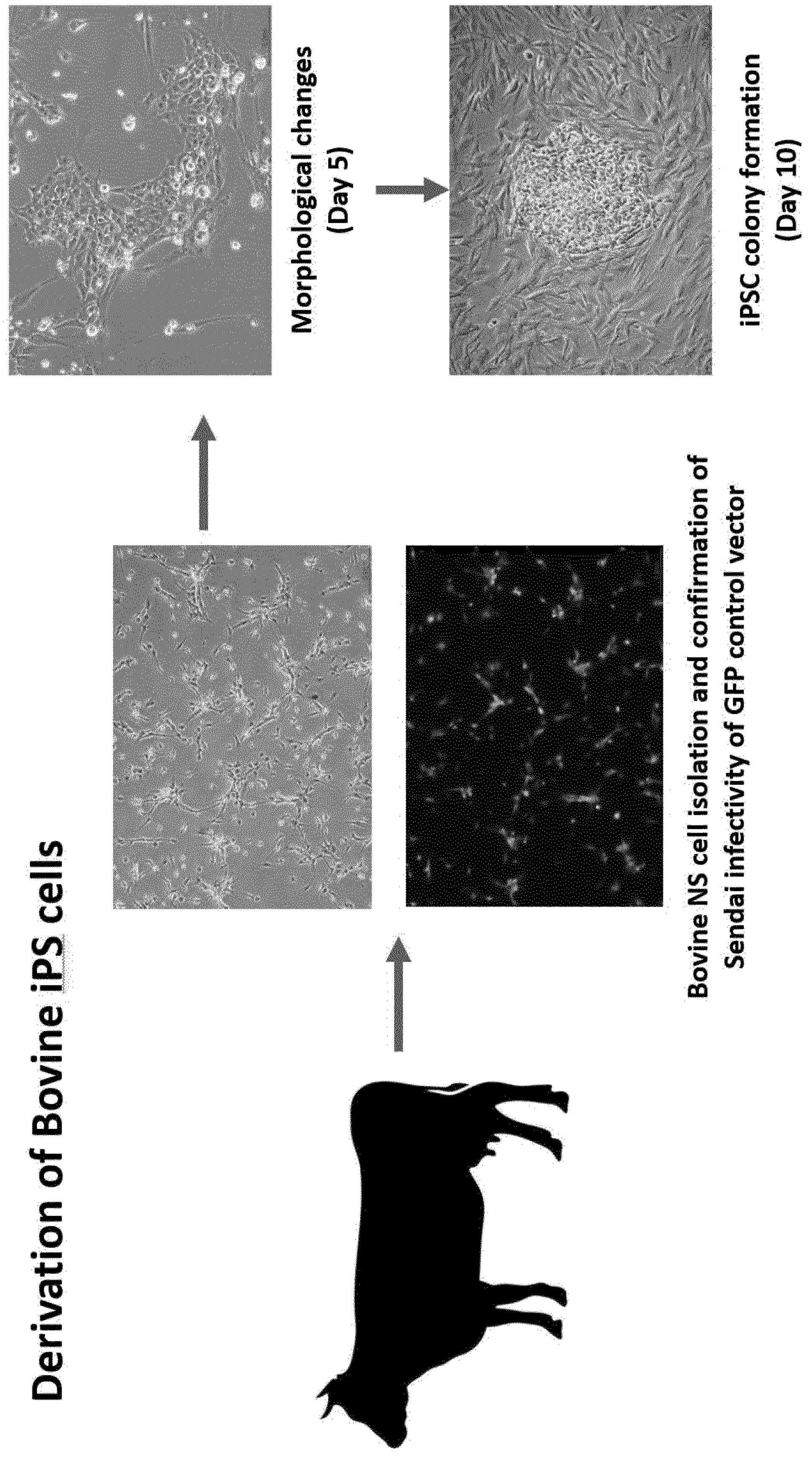
FIG. 9 shows the derivation of bovine NSCs and subsequent reprogramming into iPSCs.

FIG. 9 illustrates both the derivation of bovine NSCs and their subsequent reprogramming into iPSCs.

Example 7—iPSC Marker Confirmation

The iPSC induction method of the invention (as demonstrated in Examples 4, 5 and 6) was found to be highly efficient and generate thousands of iPSC clones from dog NSCs (Example 4), pig NSCs (Example 5) and cow NSCs (Example 6) in a manner not achievable with Sendai infection under standard conditions.

Figure 2:
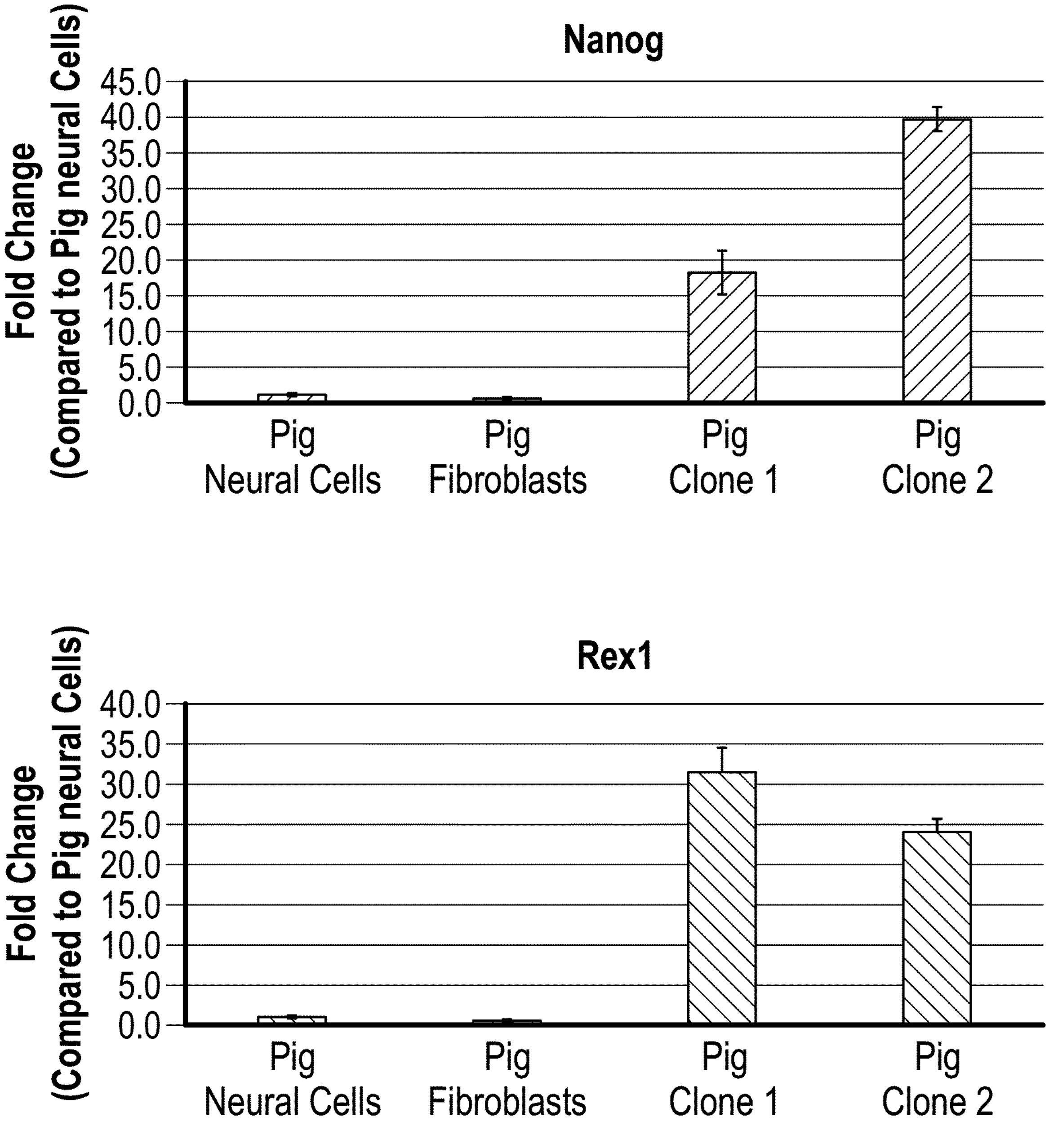
FIG. 2 shows NANOG and REX1 expression in porcine iPSCs.

The colonies generated using this method had discrete edges and morphology typical of pluripotent stem cells. They could be easily cloned by picking, were positive for stem cell markers such as homogenous alkaline phosphatase expression and Oct4, as well as having increased expression of the pluripotency markers NANOG and REX1 (see FIG. 1 for canine iPSCs and FIG. 2 for porcine iPSCs).

Figure 3:
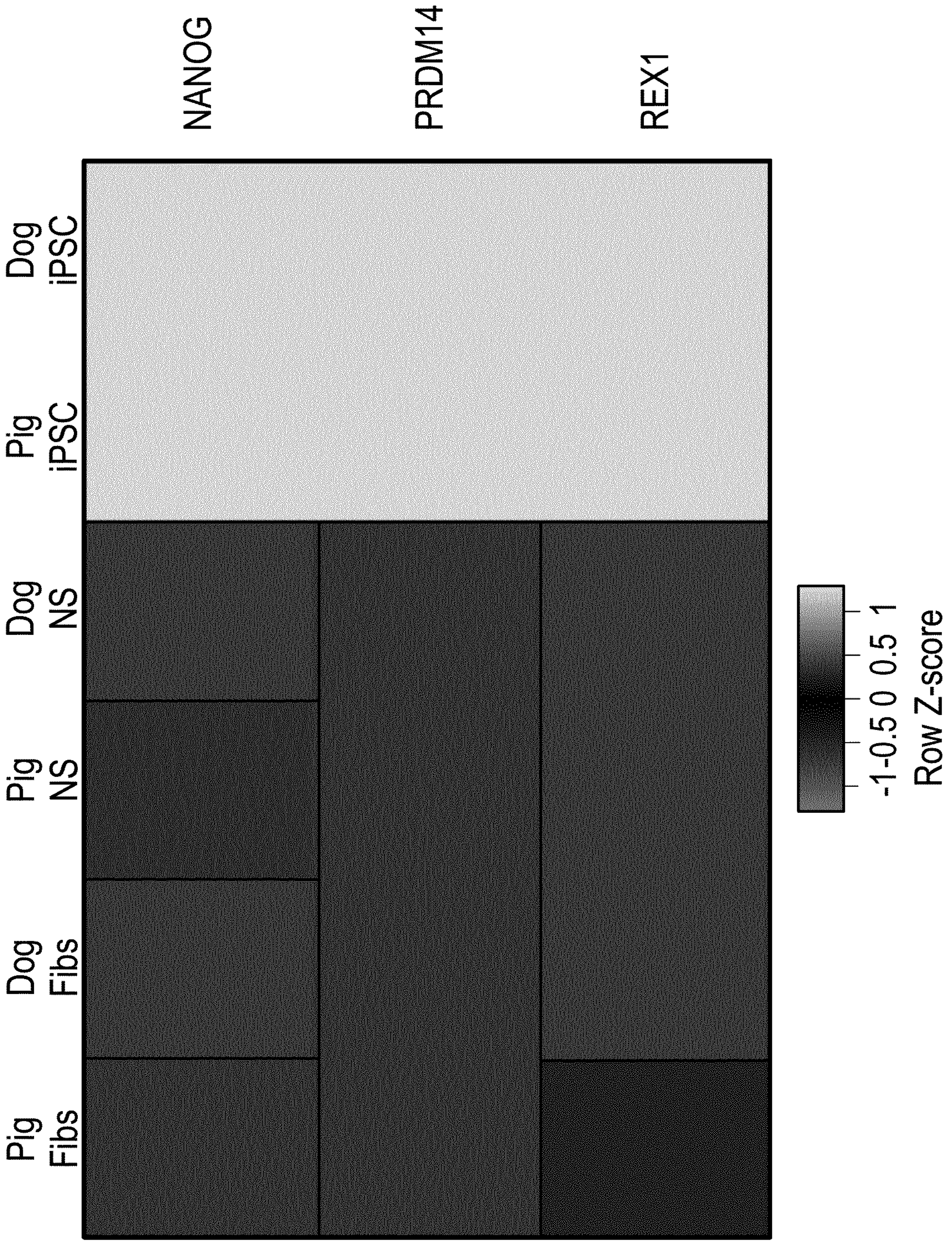
FIG. 3 shows a heat map of pluripotent stem cell marker expression.

FIG. 3 is a heat map showing expression of the pluripotent stem cell markers for canine and porcine fibroblasts, NSCs and iPSCs, it clearly indicates that NANOG, PRDM14 and REX1 are all expressed at much higher levels in the iPSCs than in either of the other cell types.

Figure 4:
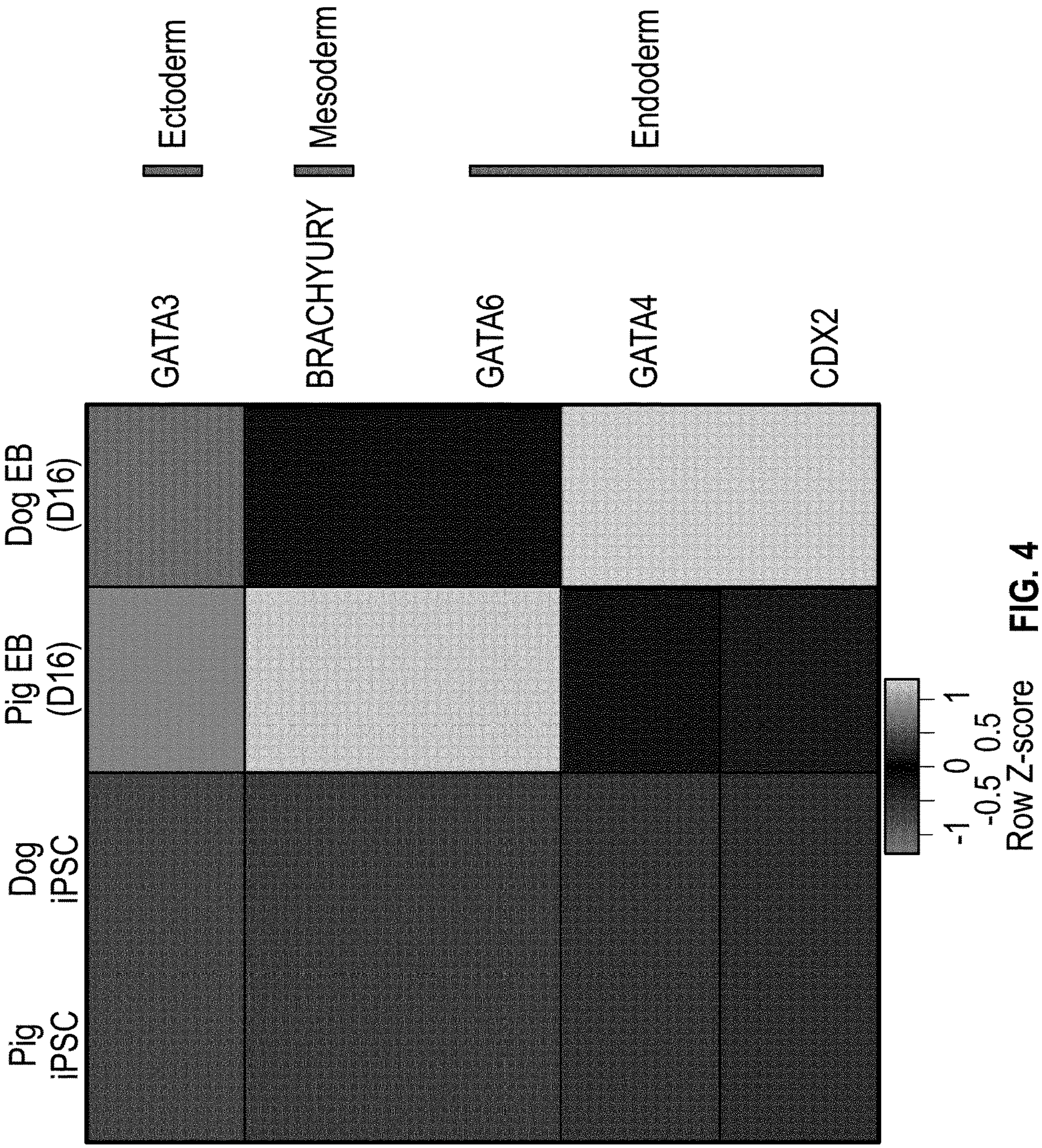
FIG. 4 shows a heat map of somatic cell marker expression.

FIG. 4 is a heat map showing expression of somatic cell markers of endoderm (GATA6, GATA4 and CDX2), ectoderm (GATA3) and mesoderm (BRACHYURY) in canine and porcine iPSCs and embryoid bodies (EBs); it clearly indicates that, in contrast to the EBs, somatic cell markers are expressed only at very low levels by the iPSCs.

Example 8—Determination of SSEA-3 and SSEA-4 Marker Profiles

Figure 5:
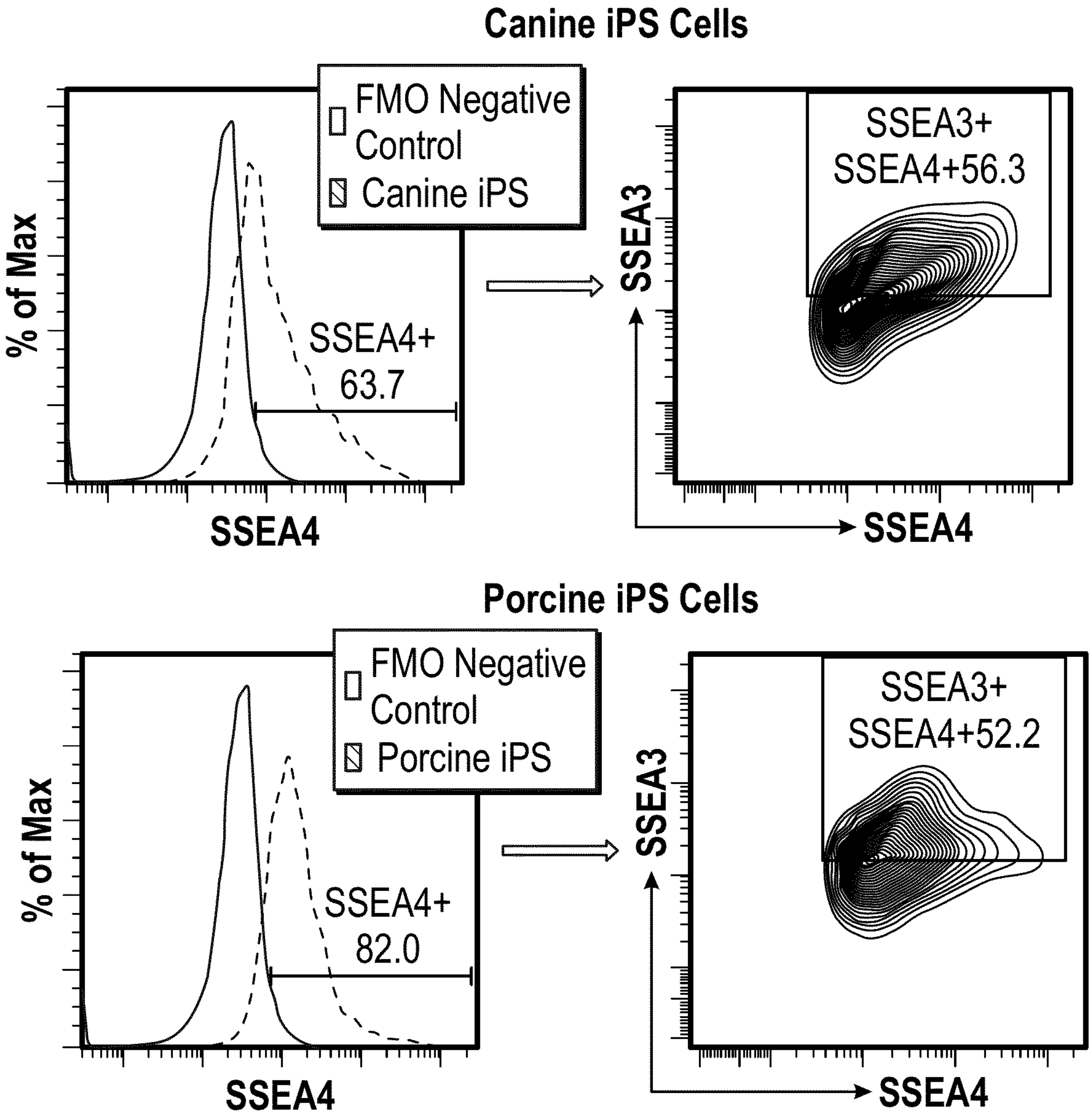
FIG. 5 shows SSEA-3 and SSEA-4 marker profiles for iPSCs of the invention.

Canine and porcine iPSCs prepared as per above examples were disaggregated into single cells and stained with antibodies specific for two cell surface antigens associated with pluripotency in human iPSCs (SSEA-3 and SSEA-4). The flow cytometry results are shown in FIG. 5: upper two panels=canine iPSCs, lower two panels=porcine iPSCs.

In excess of 60% of canine iPSCs and in excess of 80% of porcine iPSCs were positive for SSEA-4 expression, while of that SSEA-4$^+$ population of iPSCs in excess of 55% of the canine iPSCs were also SSEA-3$^+$ and in excess of 50% of the porcine iPSCs were also SSEA-3$^+$. Furthermore, the iPSC populations analyzed for SSEA-3 and -4 expression were impure, as they also included MEFs (negative for each of the markers) from the culture medium, and hence the SSEA-3 and -4 marker expression in the canine and porcine iPSCs is likely undervalued in this experiment.

Furthermore, at the time of first writing this Example, the iPSCs have been maintained for over a year in culture. These iPSCs have been passaged extensively and have been successfully cloned and subcloned multiple times without difficultly. It has also been found that the iPSCs can be differentiated to form EBs, express differentiation markers and undergo directed differentiation into all three cell lineages (ecto-, endo- and meso-derm). RNAseq data demonstrates that both canine and porcine iPSCs generated according to the invention have endogenous gene expression consistent with a common self-renewing phenotype.

Example 9—Derivation of iPSCs from Porcine Cells (Fibroblast Vs NSC)

Figure 6:
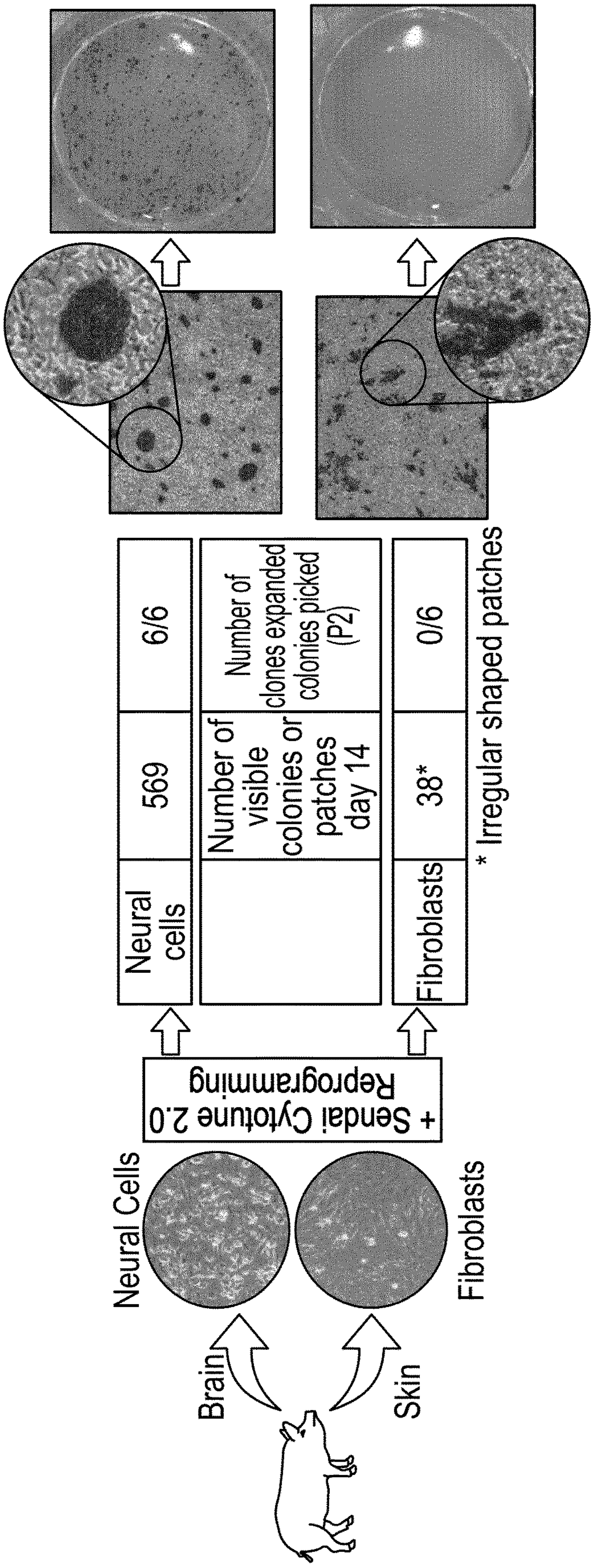
FIG. 6 shows the difference in iPSC induction efficacy when starting from porcine neural stem cells compared to porcine fibroblasts.

As can be seen in FIG. 6, biopsies were taken from the skin and brain from the same piglet. Fibroblast and neural stem cell cultures were separately established and reprogrammed with Sendai Cytotune 2.0 reprogramming kit (Thermo Fisher).

Visible colonies were counted at day 14; smooth edged colonies were observed on neural cell reprogramming plates while irregular cell patches were seen on fibroblast plates.

Alkaline phosphatase staining of reprogramming plates showed uniform staining of neural derived iPS colonies (569 colonies counted), and irregular-shaped stained patches on fibroblast reprogramming plates (38 patches counted).

All six colonies picked from neural reprogrammed cells established iPS cell lines after picking and passaging (stained with Alkaline Phosphatase), while none of six picked fibroblast patches established iPS cell clones (none stained with Alkaline Phosphatase).

This showed success in generating iPS cells from neural stem cells of the pig but not from skin fibroblast cells.

Example 10—Derivation of iPSCs from Porcine Neural Stem Cells Using Oct4

Figure 7:
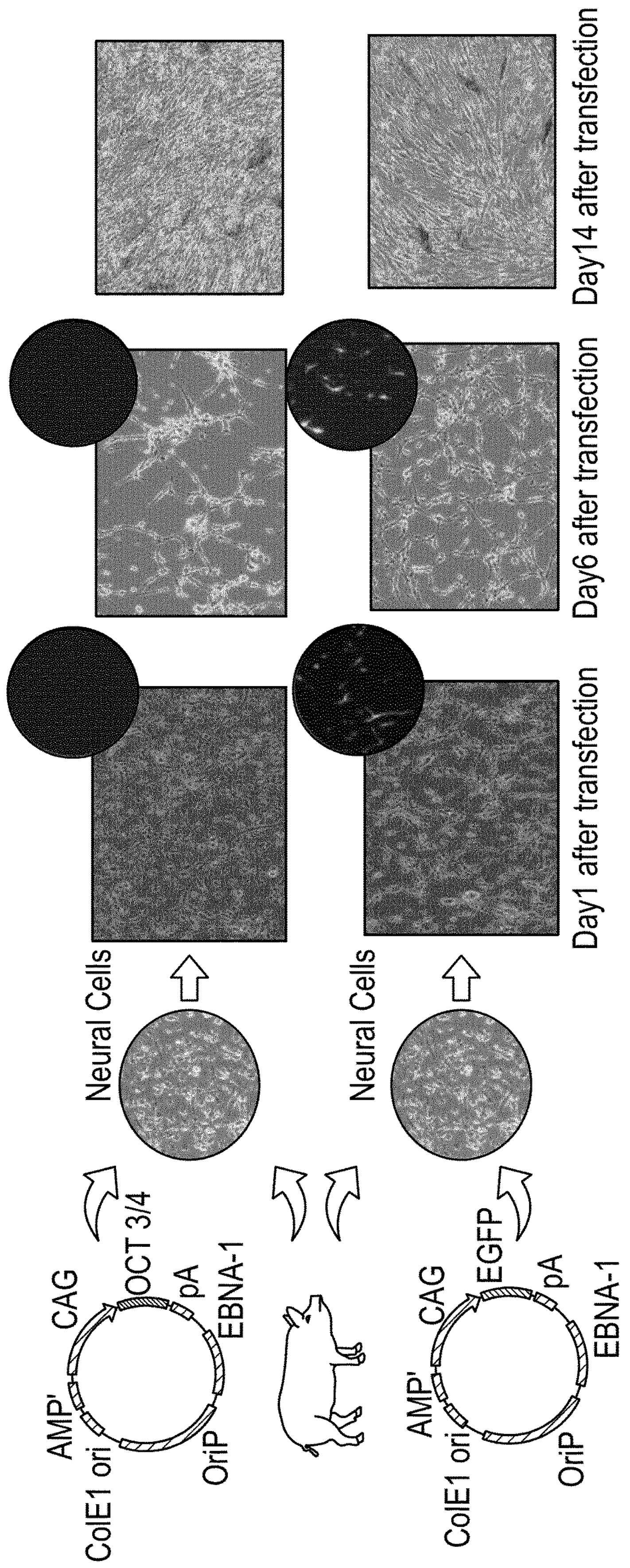
FIG. 7 shows the inability of Oct4 alone to induce reprogramming of porcine neural stem cells into iPSCs.

As can be seen in FIG. 7, either Oct4 or eGFP episomal plasmids were transfected into porcine neural stem cells.

Expression from the vectors was confirmed by fluorescence from GFP vector within 24 hrs of transfection.

Sustained expression of the constructs was confirmed through GFP expression by day 6 after transfection. By day 6 cultures transfected with Oct4 episome showed increased cell death as well as morphological changes in the appearance of cells including the formation of clusters.

Transfected cells were replated onto feeders in stem cell media on day 7 after transfections. On day 14 after transfection no iPS like colonies were visible on either GFP or Oct4 transfected conditions. Staining with alkaline phosphatase showed some spindle like positive stained cells within both GFP and Oct4 cultures; however, no iPS cell colonies were present. This showed Oct 4 alone was insufficient to generate iPS cells from neural stem cells of the pig.

Example 11—Gene Expression Profiling

By performing an RNA-sequencing (RNAseq) analysis, a series of genes known to be implicated in pluripotency were identified; these genes being common to the iPSCs of the invention and other iPSCs (for which RNAseq data is publicly available). These genes include endogenous OCT4, NANOG, STAT3, REX1 and PDMR14.

This RNAseq analysis confirmed that the iPSCs of the invention share all the expression patterns of known ground-state iPSC populations. Gene expression was confirmed by qRT-PCR.

In addition to the above gene expression pattern, a number of uniquely expressed genes were identified in the iPSCs of the invention. RNAseq datasets were compared to provide a list of differentially expressed genes (adjusted p value<0.1) by pairwise comparison of pig iPSCs according to the invention vs other publicly available pig iPSC paired-end RNAseq datasets (see NCBI Short Read Archive; Run Accession Numbers: DRR124546, DRR124547, DRR161385, DRR161386, ERR3153959, ERR3153960, SRR10677611, SRR10677612, SRR10677613, SRR10677614, SRR10677615, SRR10677616, SRR10677617, SRR10677618, SRR10677619, SRR10677620, SRR10677621, SRR10677622, SRR4296448, SRR4296449, SRR4296450, SRR4296451, SRR5130116, SRR5130117, SRR5130118, SRR5130119, SRR5130120, SRR5130121, SRR8539521, SRR8539522, SRR8539523, SRR8539524, SRR8539525, SRR8539526, SRR8539527 and SRR8539528).

In total, 21 differentially expressed genes were retained (adjusted p value<0.1). These genes included GLDN, PTK2B, LOC110260197, ANGPT1, LY96, NYAP2, THBS2, ULK4, CRSP3, CHST8, SKOR1, KCNMB2, LMNA, HTRA1, PHLDA1, FGF1 and GASK1B.

From the 21 differentially expressed genes, 5 genes were identified as also been highly expressed in the canine iPS cells. These differentially expressed genes include high levels of expression of LMNA, HTRA1, PHLDA1, FGF1 and GASK1B as unique markers of the iPSCs of the invention. As is known in the art, these genes have diverse functions from DNA repair, tumour suppression and cell growth, all of which may contribute to sustained growth and subsequent differentiation potential.

Figure 8:
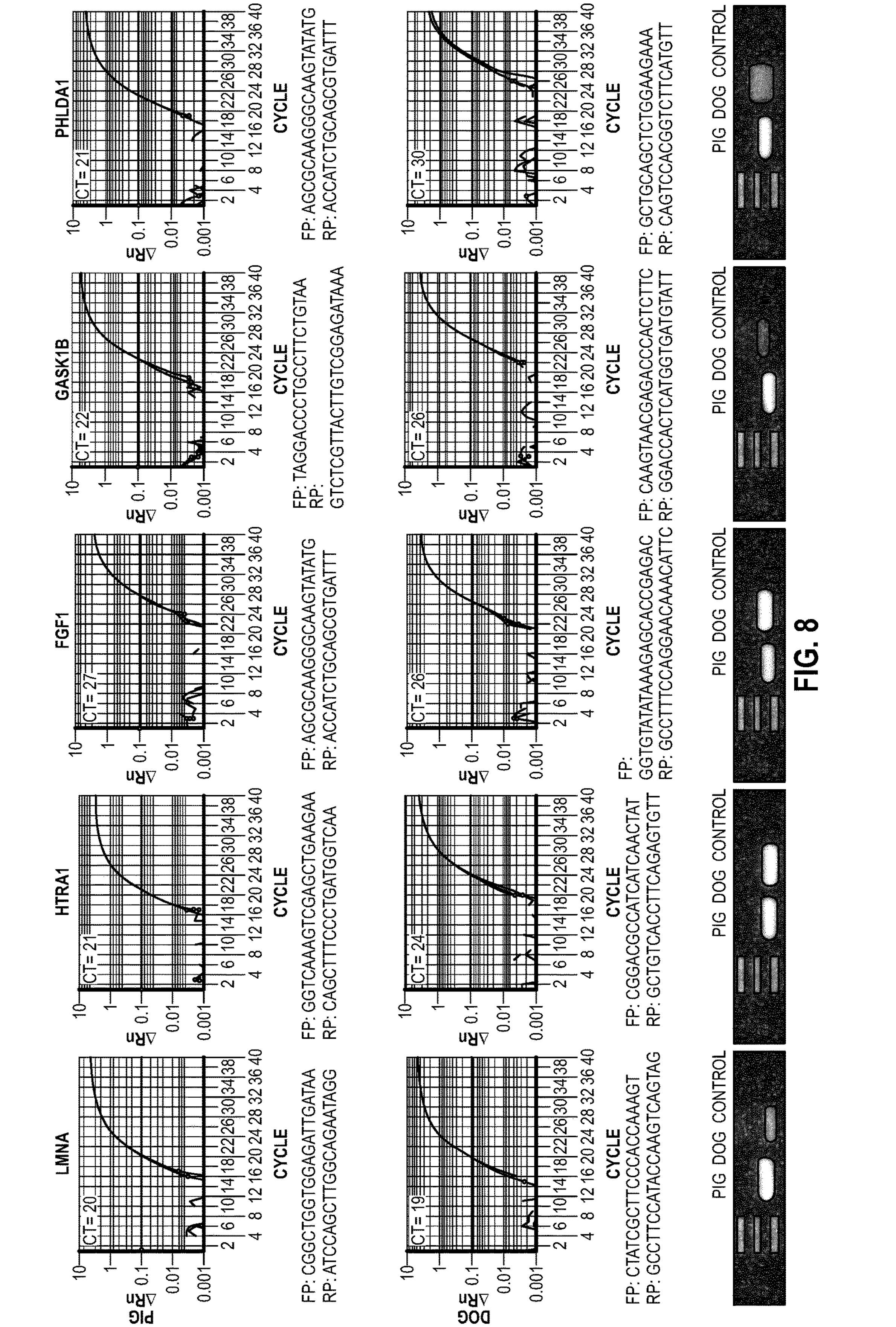
FIG. 8 shows confirmation of gene expression patterns in porcine and canine iPSCs found to be differentially expressed in RNAseq studies.

The 5 genes (LMNA, HTRA1, PHLDA1, FGF1 and GASK1B) were additionally found to be expressed in the canine and porcine iPSCs of the invention, as confirmed by RT-PCR and qRT-PCR. FIG. 8 shows standard RT-PCR demonstrating the expression of LMNA, HTRA1, FGF1 GASK1B and PHLDA1 in both porcine and canine iPSCs and confirmation via qPCR with calculated CT values. Primers used are shown below each graph. Appropriate gene expression controls were used to validate and normalize the expression of these genes.

The invention thus provides a method of inducing pluripotency in a cell of lower relative potency that is derived from a domestic animal or a farm animal.

The invention claimed is:

1. A porcine induced pluripotent stem cell (iPSC), wherein the iPSC is derived from a neural stem cell (NSC) and expresses genes LMNA, HTRA1, PHLDA1, FGF1 and GASK1B.

2. The porcine iPSC according to claim 1, wherein the iPSC additionally expresses genes NANOG, REX1, SSEA-3 and SSEA-4.

3. A population of porcine iPSCs, wherein at least 50% of the iPSCs express genes LMNA, HTRA1, PHLDA1, FGF1 and GASK1B, and wherein the population is derived from NSCs.

4. The population according to claim 3, wherein at least 90% of the iPSCs express genes LMNA, HTRA1, PHLDA1, FGF1 and GASK1B.

5. The population according to claim 3, wherein at least 95% of the iPSCs express genes LMNA, HTRA1, PHLDA1, FGF1 and GASK1B.

6. A method of inducing pluripotency, comprising culturing porcine neural stem cells (NSCs) in the presence of non-integrating vectors that express one or more reprogramming factors, wherein the method produces porcine iPSCs that express genes LMNA, HTRA1, PHLDA1, FGF1 and GASK1B.

7. The method according to claim 6, wherein the reprogramming factors are Oct4, Sox2, cMyc and Klf4.

8. The method according to claim 6, wherein the vectors are Sendai viral vectors.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Primer Sequence

<400> SEQUENCE: 1

cggctggtgg agattgataa                                          20
```

<210> SEQ ID NO 2
<211> LENGTH: 20
<212> TYPE: DNA
<213> ORGANISM: Artificial Sequence
<220> FEATURE:
<223> OTHER INFORMATION: Primer Sequence

<400> SEQUENCE: 2
atccagcttg gcagaatagg 20

<210> SEQ ID NO 3
<211> LENGTH: 20
<212> TYPE: DNA
<213> ORGANISM: Artificial Sequence
<220> FEATURE:
<223> OTHER INFORMATION: Primer Sequence

<400> SEQUENCE: 3
ctatcgcttc ccaccaaagt 20

<210> SEQ ID NO 4
<211> LENGTH: 22
<212> TYPE: DNA
<213> ORGANISM: Artificial Sequence
<220> FEATURE:
<223> OTHER INFORMATION: Primer Sequence

<400> SEQUENCE: 4
gccttccata ccaagtcagt ag 22

<210> SEQ ID NO 5
<211> LENGTH: 21
<212> TYPE: DNA
<213> ORGANISM: Artificial Sequence
<220> FEATURE:
<223> OTHER INFORMATION: Primer Sequence

<400> SEQUENCE: 5
ggtcaaagtc gagctgaaga a 21

<210> SEQ ID NO 6
<211> LENGTH: 20
<212> TYPE: DNA
<213> ORGANISM: Artificial Sequence
<220> FEATURE:
<223> OTHER INFORMATION: Primer Sequence

<400> SEQUENCE: 6
cagctttccc tgatggtcaa 20

<210> SEQ ID NO 7
<211> LENGTH: 20
<212> TYPE: DNA
<213> ORGANISM: Artificial Sequence
<220> FEATURE:
<223> OTHER INFORMATION: Primer Sequence

<400> SEQUENCE: 7
cggacgccat catcaactat 20

<210> SEQ ID NO 8
<211> LENGTH: 20
<212> TYPE: DNA
<213> ORGANISM: Artificial Sequence
<220> FEATURE:
<223> OTHER INFORMATION: Primer Sequence

<400> SEQUENCE: 8
gctgtcacct tcagagtgtt 20

<210> SEQ ID NO 9
<211> LENGTH: 20
<212> TYPE: DNA
<213> ORGANISM: Artificial Sequence
<220> FEATURE:
<223> OTHER INFORMATION: Primer Sequence

<400> SEQUENCE: 9
agcgcaaggg caagtatatg 20

<210> SEQ ID NO 10
<211> LENGTH: 19
<212> TYPE: DNA
<213> ORGANISM: Artificial Sequence
<220> FEATURE:
<223> OTHER INFORMATION: Primer Sequence

<400> SEQUENCE: 10
accatctgca gcgtgattt 19

<210> SEQ ID NO 11
<211> LENGTH: 24
<212> TYPE: DNA
<213> ORGANISM: Artificial Sequence
<220> FEATURE:
<223> OTHER INFORMATION: Primer Sequence

<400> SEQUENCE: 11
ggtgtatata aagagcaccg agac 24

<210> SEQ ID NO 12
<211> LENGTH: 22
<212> TYPE: DNA
<213> ORGANISM: Artificial Sequence
<220> FEATURE:
<223> OTHER INFORMATION: Primer Sequence

<400> SEQUENCE: 12
gcctttccag gaacaaacat tc 22

<210> SEQ ID NO 13
<211> LENGTH: 20
<212> TYPE: DNA
<213> ORGANISM: Artificial Sequence
<220> FEATURE:
<223> OTHER INFORMATION: Primer Sequence

<400> SEQUENCE: 13
taggaccctg ccttctgtaa 20

<210> SEQ ID NO 14
<211> LENGTH: 24
<212> TYPE: DNA
<213> ORGANISM: Artificial Sequence
<220> FEATURE:
<223> OTHER INFORMATION: Primer Sequence

<400> SEQUENCE: 14
gtctcgttac ttgtcggaga taaa 24

<210> SEQ ID NO 15
<211> LENGTH: 22

<212> TYPE: DNA
<213> ORGANISM: Artificial Sequence
<220> FEATURE:
<223> OTHER INFORMATION: Primer Sequence

<400> SEQUENCE: 15
caagtaacga gacccactct tc 22

<210> SEQ ID NO 16
<211> LENGTH: 22
<212> TYPE: DNA
<213> ORGANISM: Artificial Sequence
<220> FEATURE:
<223> OTHER INFORMATION: Primer Sequence

<400> SEQUENCE: 16
ggaccactca tggtgatgta tt 22

<210> SEQ ID NO 17
<211> LENGTH: 20
<212> TYPE: DNA
<213> ORGANISM: Artificial Sequence
<220> FEATURE:
<223> OTHER INFORMATION: Primer Sequence

<400> SEQUENCE: 17
agcgcaaggg caagtatatg 20

<210> SEQ ID NO 18
<211> LENGTH: 19
<212> TYPE: DNA
<213> ORGANISM: Artificial Sequence
<220> FEATURE:
<223> OTHER INFORMATION: Primer Sequence

<400> SEQUENCE: 18
accatctgca gcgtgattt 19

<210> SEQ ID NO 19
<211> LENGTH: 19
<212> TYPE: DNA
<213> ORGANISM: Artificial Sequence
<220> FEATURE:
<223> OTHER INFORMATION: Primer Sequence

<400> SEQUENCE: 19
gctgcagctc tggaagaaa 19

<210> SEQ ID NO 20
<211> LENGTH: 20
<212> TYPE: DNA
<213> ORGANISM: Artificial Sequence
<220> FEATURE:
<223> OTHER INFORMATION: Primer Sequence

<400> SEQUENCE: 20
cagtccacgg tcttcatgtt 20